(12) United States Patent
Harder et al.

(10) Patent No.: US 6,416,517 B2
(45) Date of Patent: *Jul. 9, 2002

(54) REAMING TOOL FOR REAMING BONE CANALS

(75) Inventors: Hans E. Harder, Probsteirhagen (DE); Seyed-Mehdi Mousavi; Vilmos Vécsei, both of Vienna (AT)

(73) Assignee: Stryker Trauma GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/128,916

(22) Filed: Aug. 4, 1998

(30) Foreign Application Priority Data

Aug. 4, 1997 (DE) .......................... 297 13 897

(51) Int. Cl.⁷ ............................................... A61B 17/16
(52) U.S. Cl. ......................... 606/80; 408/230; 606/180
(58) Field of Search .............................. 606/79, 80, 81, 606/170, 180; 408/230

(56) References Cited

U.S. PATENT DOCUMENTS

| 3,081,635 A | | 3/1963 | Bowers |
|---|---|---|---|
| 3,180,379 A | | 4/1965 | Stewart |
| 3,667,857 A | * | 6/1972 | Shaner et al. ................ 408/230 |
| 4,507,028 A | * | 3/1985 | Matsushita .................. 408/230 |
| 4,549,616 A | * | 10/1985 | Rumpp et al. .............. 408/230 |
| 4,751,922 A | | 6/1988 | DiPietropolo |
| 4,811,800 A | * | 3/1989 | Hill et al. |
| 4,936,313 A | | 6/1990 | Burkhardt et al. |
| 5,122,134 A | * | 6/1992 | Borzone et al. .............. 606/80 |
| 5,148,877 A | * | 9/1992 | MacGregor |
| 5,462,130 A | | 10/1995 | Peetz |
| 5,891,148 A | * | 4/1999 | Deckner ...................... 606/80 |
| 5,908,423 A | | 6/1999 | Kashuba et al. |

FOREIGN PATENT DOCUMENTS

| DE | 2542056 | 3/1977 |
|---|---|---|
| DE | 19528242 | 6/1997 |
| EP | 0 253 526 | 10/1995 |
| FR | 1280241 | 5/1962 |

* cited by examiner

Primary Examiner—David O. Reip
(74) Attorney, Agent, or Firm—Lerner, David, Littenberg, Krumholz & Mentlik, LLP

(57) ABSTRACT

A reaming tool for reaming bone canals with a drill head which is mounted on an elongate flexible shaft which has a diameter smaller than that of the drill head and be which can be connected to a rotary drive motor, wherein the drill head and shank comprise a through-bore for a guiding wire wherein the shaft at least over a part of its length is spiraled in a thread-like manner.

7 Claims, 1 Drawing Sheet

REAMING TOOL FOR REAMING BONE CANALS

BACKGROUND OF THE INVENTION

1. Field of the Invention

The invention relates to a reaming tool for reaming bone canals.

2. Description of the Related Art

Such reaming tools are applied in tubular bones, for example with the femur, for applying a hip joint prosthesis or before driving in a bone nail for the femur, tibia, humerus, etc. From EP 0 508 710 there is known a reaming tool which consists of a drill head and an elongate shank which can be connected thereto. The drill head consists of four teeth arranged at a 90° distance with a chamfer which furthermore comprises a central through-bore. The shank, which is likewise drilled through has a smaller diameter than the drill head. The central through-bore of the shank and drill head serves for accommodating a guiding wire along which the reaming tool is driven forward.

From EP 0 440 377 there is further known a reaming tool which comprises a modified drill head and a shank which is formed flexibly. With the help of the flexible shank which at the same time represents a flexible shaft the drill head may also be moved along an arcuate path, which is required in many cases. For such a flexible shaft there are various known designs. They must not only be flexible but also be able to transmit a suitable torque.

On application, the chips removed away from the bone are conveyed behind the drill head into the intermediate space between the shank and the canal. With longer drillings it is therefore necessary to remove the tool from the canal from time to time in order to remove the chips. In this way the operating time is drastically increased. If the removal of the chips is not effected in time, a blockage of chips may occur with a corresponding blocking up of the drill head by which means an unallowable loading of the bone may occur, in particular by the developing heat.

SUMMARY OF THE INVENTION

It is therefore the object of the invention to provide a reaming tool for drilling bone canals with which the removal of chips is significantly improved.

This object is achieved by the device of the invention.

With the reaming tool according to the invention, the shank is at least over a part of its length spiraled in the manner of a thread. Preferably, the spiraling extends over the whole length of the shank, at least over a length such that the spiraled section is still located outside the bone when the drill head is in its furthest driven in position.

Although the outer diameter of the spiraled shank, for obvious reasons, is clearly smaller than the outer diameter of the drill head, it is possible with such a flexible shank to convey a sufficiently large part of the machined chips to the outside. Under certain circumstances all temporary removal of the drill head from the drilled out canal, for the purpose of chip removal, is done away with, however at least the number of such procedures is limited to a minimum.

In order to prevent damage to the canal walls, one form therefor of the invention provides for the thread tip to be flattened or rounded.

Although it is conceivable to form the shank of metal, it may be manufactured just as well from plastic.

BRIEF DESCRIPTION OF THE DRAWINGS

One embodiment form of the invention is described in more detail by way of the drawings.

DETAILED DESCRIPTION OF THE PREFERRED EMBODIMENTS

Figure 1:
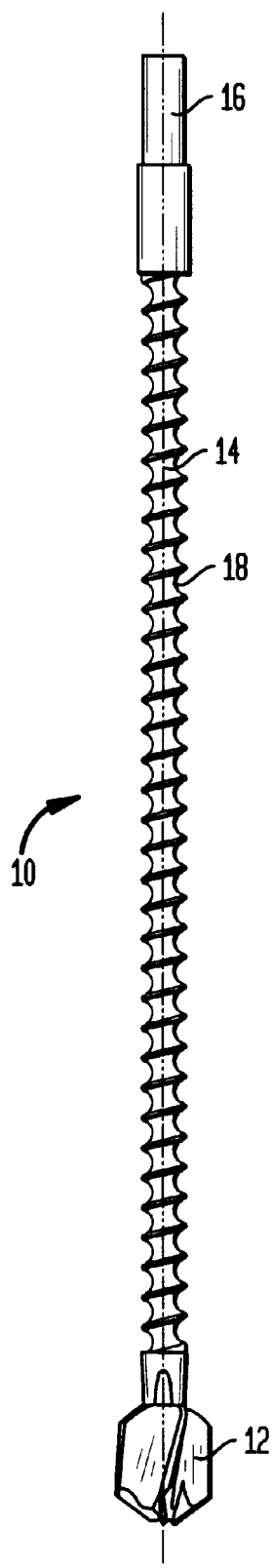
FIG. 1 schematically shows a reaming tool according to the invention.

In FIG. 1 there is illustrated a reaming tool at 10. It comprises a drill head 12 which e.g. may be formed according to EP 0 508 710 or according to WO 97/03617. A flexible shank 14 is connected to the drill head 12. The connection is not shown in detail. It may be conventional. Preferably there is provided a releasable connection, so that e.g. a drill head with a different diameter can be connected to the shank 14. At the free end of the shank 14 there is mounted a cylindrical clamping piece 16 for connecting the shank 14 to the chuck of a rotary tool, in particular a rotary drive machine, for example an electric or pneumatic motor.

As can be recognized from the drawing, the shank 14 is spiraled in a helix-shaped manner as is shown at 18. The spiraling 18 is carried out in a thread-like or corkscrew-like manner and is provided with an adequately deep groove so that in spite of an outer diameter of the shank 14 which is significantly smaller than that of the outer diameter of the drill head 12, chips which are conveyed from the drill head 12 rearwards are transported rearwards by the spiraling of the shank 14 to the clamping piece therefor which lies safely outside the bone.

The shank 14 is formed of metal or plastic, and this being in a manner such that it can transmit the torque which is required for the reaming, but at the same time is flexible in order to function as a type of flexible shaft.

Figure 2:
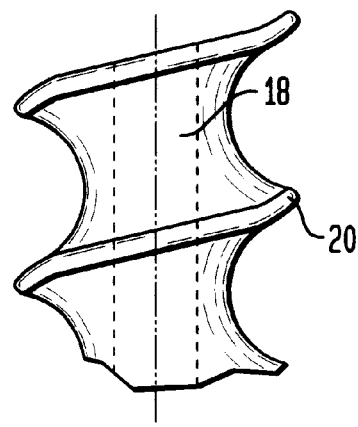
FIG. 2 shows a detail of the reaming tool according to FIG. 1.

As becomes clear from FIG. 2, the tip of the threads is rounded or flattened as is indicated at 20. In this way, on contacting or abutting the walls of the bone canal, injuries are avoided.

As previously quoted it is to be understood that the drill head 12 and the shank 14 comprise a through-bore for guiding through a guide wire, which is not shown.

What is claimed is:

1. A reaming tool for reaming bone canals and conveying cut bone chips from a first depth within the canal to an open end of the bone comprising a drill head which is mounted on an elongated flexible shank which has a diameter smaller than that of the drill head and which can be connected to a rotary drive motor, wherein the drill head and the shank comprise a through-bore for a guiding wire, and wherein the shank contains a flexible spiraled section a substantial portion over of its length that is spiraled in a thread-like manner and has an arcuate thread groove and thread tip.

2. The reaming tool according to claim 1, wherein the thread tip is rounded or flattened.

3. The reaming tool according to claim 1, wherein the shank is of plastic or metal.

4. The reaming tool according to claim 1 wherein the shank is spiraled over a length such that the spiraled section extends to said open end of the bone canal when the drill head is at said first depth.

5. A reaming tool for reaming bone canals and conveying cut bone chips from a first depth within the canal to an open end of the bone comprising a drill head mounted on a cannulated elongated flexible shank, wherein the shank has a diameter smaller than that of the drill head, and wherein the shank contains a flexible spiraled section at least over part of its length that is spiraled in a thread-like manner, the spiraled section containing an arcuate thread groove for conveying bone chips and a rounded or flattened thread tip wherein the shank is spiraled over a length such that the spiraled section extends to said open end of the bone canal when the drill head is at a said first depth.

6. The reaming tool according to claim 5 wherein the shank can be connected to a rotary drive motor.

7. The reaming tool according to claim 5 wherein the shank is of plastic or metal.

* * * * *

UNITED STATES PATENT AND TRADEMARK OFFICE
CERTIFICATE OF CORRECTION

PATENT NO. : 6,416,517 B2
DATED : July 9, 2002
INVENTOR(S) : Hans E. Harder, Vilmos Vecsei and Seyed-Mehdi Mousavi It is certified that error appears in the above-identified patent and that said Letters Patent is hereby corrected as shown below:

<u>Title page,</u>
Item [57], ABSTRACT,
Line 3, cancel "be".

<u>Column 1,</u>
Line 17, after "through" insert -- , --.
Line 23, after "shank" insert -- , --.
Line 24, after "shaft" insert -- , --.
Line 60, cancel "therefor".

<u>Column 2,</u>
Line 6, "EMBODIMENTS" should read -- EMBODIMENT --.

<u>Column 3,</u>
Line 1, after "tip" insert -- , --.

Signed and Sealed this

Twenty-eighth Day of January, 2003

JAMES E. ROGAN
*Director of the United States Patent and Trademark Office*